(12) United States Patent
Kato et al.

(10) Patent No.: US 6,884,225 B2
(45) Date of Patent: Apr. 26, 2005

(54) MEDICAL GUIDE WIRE

(75) Inventors: Tomihisa Kato, Aichi-ken (JP); Kenjiro Uematsu, Aichi-ken (JP)

(73) Assignee: Asahi Intecc Co., Ltd., Nagoya (JP)

( * ) Notice: Subject to any disclaimer, the term of this patent is extended or adjusted under 35 U.S.C. 154(b) by 164 days.

(21) Appl. No.: 10/308,169

(22) Filed: Dec. 3, 2002

(65) Prior Publication Data

US 2003/0125642 A1 Jul. 3, 2003

(30) Foreign Application Priority Data

Dec. 3, 2001 (JP) ........................................ 2001-368039

(51) Int. Cl.⁷ ........................... A61B 5/00; A61M 25/00
(52) U.S. Cl. ..................................................... 600/585
(58) Field of Search ................................ 600/585, 434; 604/525

(56) References Cited

U.S. PATENT DOCUMENTS

| | | | |
|---|---|---|---|
| 4,748,986 A | 6/1988 | Morrison et al. | |
| 5,372,144 A | 12/1994 | Mortier et al. | |
| 5,460,187 A | * 10/1995 | Daigle et al. | 600/585 |
| 5,480,382 A | 1/1996 | Hammerslag et al. | |
| 5,637,089 A | 6/1997 | Abrams et al. | |
| 5,891,055 A | 4/1999 | Sauter | |
| 6,296,616 B1 | 10/2001 | McMahon | |
| 6,602,207 B1 | * 8/2003 | Mam et al. | 600/585 |

FOREIGN PATENT DOCUMENTS

| | | |
|---|---|---|
| EP | 0 466 437 A1 | 1/1992 |
| JP | 3-60674 | 3/1991 |
| JP | 4-25024 | 4/1992 |
| JP | 09 056822 | 3/1997 |
| WO | WO 96/34635 | 11/1996 |
| WO | WO 02/05886 A1 | 1/2002 |

* cited by examiner

Primary Examiner—Max F. Hindenburg
Assistant Examiner—Brian Szmal
(74) Attorney, Agent, or Firm—Morgan Lewis & Bockius LLP

(57) ABSTRACT

In a medical guide wire (1), a rigid portion (4A) is located at a distal end of a helical spring (4), and the rigid portion (4A) measures 0.5 mm or less which extends from a top end of a head plug (5) to a rear end of a portion in which the helical spring (4) is secured to the head plug (5), and an intermediary location (11) is secured to an intermediary boss portion (9) of a core line (3) to provide a loosely wound portion (8) from a rear end of the head plug (5) to the intermediary location (11) to be elastically expandable due to a clearence (C) appeared between line element turns of the loosely wound portion (8).

9 Claims, 8 Drawing Sheets

MEDICAL GUIDE WIRE

BACKGROUND OF THE INVENTION

1. Field of the Invention

The invention relates to a medical guide wire used upon introducing a catheter into a cardiovascular system or the like.

2. Description of Prior Art

A medical guide wire, in the form of a flexible line wire, is disclosed in Japanese Provisional Publication No. 4-25024 to ensure a safety insertion for a catheter when inserting a balloon catheter into a blood vessel to treat a diseased area such as angiostenosis of the coronary artery or when inserting a thin flexible catheter into the blood vessel for an angiography.

Japanese Laid-open Patent Application No. 3-60674 discloses a medical guide wire in which a core shaft has a ball-like head portion to engage with an open end section of a catheter to prevent its forward movement. The ball-like head portion has an advantage that enables a manipulator to withdraw the guide wire together with the catheter.

As shown in FIG. 15, the medical guide wire 30 is in the form of a flexible thin line having a main wire portion 31, and inserted from its front distal portion 32 into a complicatedly twisted, turned or bifurcated blood vessel while pushing, pulling and turning a handling knob 33 placed outside a patient. This requires highly improved mechanical properties for the medical guide wire 30. It is especially indispensable for a front end portion 30A to have a high flexibility and restoring force enough to return back from the deformation because the front end portion 30A plays a leading part to introduce the medical guide wire 30 into the vascular tract. For this reason, a head plug 35 is fixed to a tip of a thin core line 34, and a front portion of a helical spring 36 is provided around the core line 34 to be soldered to the head plug 35. As an alternative, a molten solder attached to the core line 34 and the helical spring 36 to form the head plug 35 is presented as a main stream structure.

In the medical guide wire 30 in which the helical spring 36 is soldered to the head plug 35, a molten soldering material inevitably adheres to the helical spring 36 and clogs a clearance 37 between line element turns of the helical spring 36 due to dispersion and sputter caused from a capillary phenomenon of the molten soldering material during the soldering operation. For this reason, a rigid 30B portion appears to extend approximately by 1.5 mm from a top of the head plug 35 to a distal end of the helical spring 36 as shown at L5.

Meanwhile, upon inserting the medical guide wire 30 into a blood vessel 37 (FIG. 16) to introduce its leading portion 32 to a diseased area such as, for example, an angiostenosis area P, whether or not a manipulator should advance the leading portion 32 is judged after confirming that the leading portion 32 is normally inserted into a true lumen (intrinsic vascular tract lumen) safely enough to pierce the diseased area by visually confirming the leading portion 32 on a monitored image and a finger tip feeling information transmitted when a manipulator pushes, pulls and turns the handling knob 33. In this instance, the leading portion 32 transmits to the handling knob 33 that there is a difference in resistance between a central hard tissue of the angiostenosis area P and an inner wall of the normal intima 38 as the information of scratching and scraggy feelings. The feelings transmitted to the handling knob 33 is a clue formation to decide whether or not the leading portion 32 is normally in the true lumen to be further advanced.

In the prior structure, due to the extended rigid portion, the leading portion lacks a flexibility which fails to transmit an exact feeling information so that the leading portion 32 may be led astray into a false lumen by penetrating through the intima 38 to reach the media 39 of the vascular tract. Once led astray into the false lumen, the leading portion 32 has a danger of piercing through the adventitial coat 40 out of the vascular tract, and the manipulator will find it difficult to return the leading portion 32 back to the true lumen as well as to exlore a new route back to the true lumen. This becomes a great hindrance to treating and curing the diseased area particularly when considering the possibility that the false lumen is dilated.

Therefore, the present invention has made with the above drawbacks in mind, it is a main object of the invention to provide a medical guide wire which is capable of inserting a front distal portion normally into a true lumen without being led astray, thereby contributing to treating and curing a diseased area quickly with high precision.

SUMMARY OF THE INVENTION

According to the present invention, there is provided a medical guide wire in which a length of a rigid portion is exceedingly reduced at a distal end of a helical spring. An elastically expandable portion extends rearward from the rigid portion to increase a flexibility of a front distal portion of the helical spring. The structure is such that the front distal portion of the medical wire is improved at its flexibility to enhance an operable feeling transmitted from the front distal portion of the helical spring upon advancing the front distal portion into a blood vessel.

In order to reduce the length of the rigid portion of the helical spring, the helical spring is secured to a head plug by means of a TIG welding, laser spot weling or the like. The rigid portion extends lengthwisely from a top of the head plug to a rear end of a portion in which the helical spring is secured to the head plug. The length of the rigid portion measures 0.5 mm or less (preferably by 0.2 mm or less).

A loosely wound portion extends as an elastically expandable portion from the rigid portion. The elastically expandable portion measures approximately 24 mm in length so as to exceed an entire length of the generally predictable diseased area. A width of a clearance appeared between line element turns of the loosely wound portion its 10% or more of a line diameter of the helical spring. A function panel-test based on a sample piece shows that a feeling of the handling knob abruptly deteriorates when the clearance reduces to less than 10% of the line diameter of the helical spring. This is a reason why 10% of the line diameter of the helical spring is defined as a lower limit of the clearance.

With a technical concept in mind that the head plug advances smoothly into the diseased area of the non-uniform vascular tract in combination with a manipulation of the medical guide wire, the head plug forms a spherical or semi-spherical configuration, and right and left side portions of the head plug are in part undercut to form flat surface portions in order to reduce a resistance that the head plug receives when advancing along the vascular tract, thereby improving a directional maneuverability of the head plug. In order to further improve the directional maneuverability of the head plug, a core line member is rectangular in cross section, longer sides of which position in parallel with the flat surface portion of the head plug.

According to the medical guide wire thus structured, the length of the front, rigid portion is reduced and the loosely wound portion extended as rearward from the rigid portion is elastically expandable at its line element turns when an outer force is applied to the loosely wound portion. The front distal portion has an elastically workable section which enhances a contact-adaptability and contact-detectability against the diseased area so as to remarkably ameliorate an operable feeling of the handling knob of the medical guide wire.

When the front distal portion is inserted into the blood vessel to be pushed, pulled and turned, the loosely wound portion meets the diseased area to elastically expand and contract the line element turns due to a contact resistance against the diseased area while admitting a soft lesion tissue of the diseased area between the line element turns of the loosely wound portion. Due to a relativity between the soft lesion tissue of the diseased area and the line element turns which admits the soft lesion tissue, an apparent change of feeling can be perceived on the handling knob to enhance a feeling precision transmitted from the loosely wound portion.

According further to the medical guide wire in which the length of the rigid portion is reduced, the front distal portion enhances a preshape capability to readily bend into a doglegged-shaped configuration substantially free from an accident in which the front distal portion is unexpectedly broken, while improving a traceability of advancing the front distal portion along a bifurcated and turned blood vessel. Other actions and effects of the present invention will be expounded in embodiments followed.

BRIEF DESCRIPTION OF THE DRAWINGS

A preferred form of the present invention is illustrated in the accompanying drawings in which.

DETAILED DESCRIPTION OF THE PREFERRED EMBODIMENTS

Figure 1:
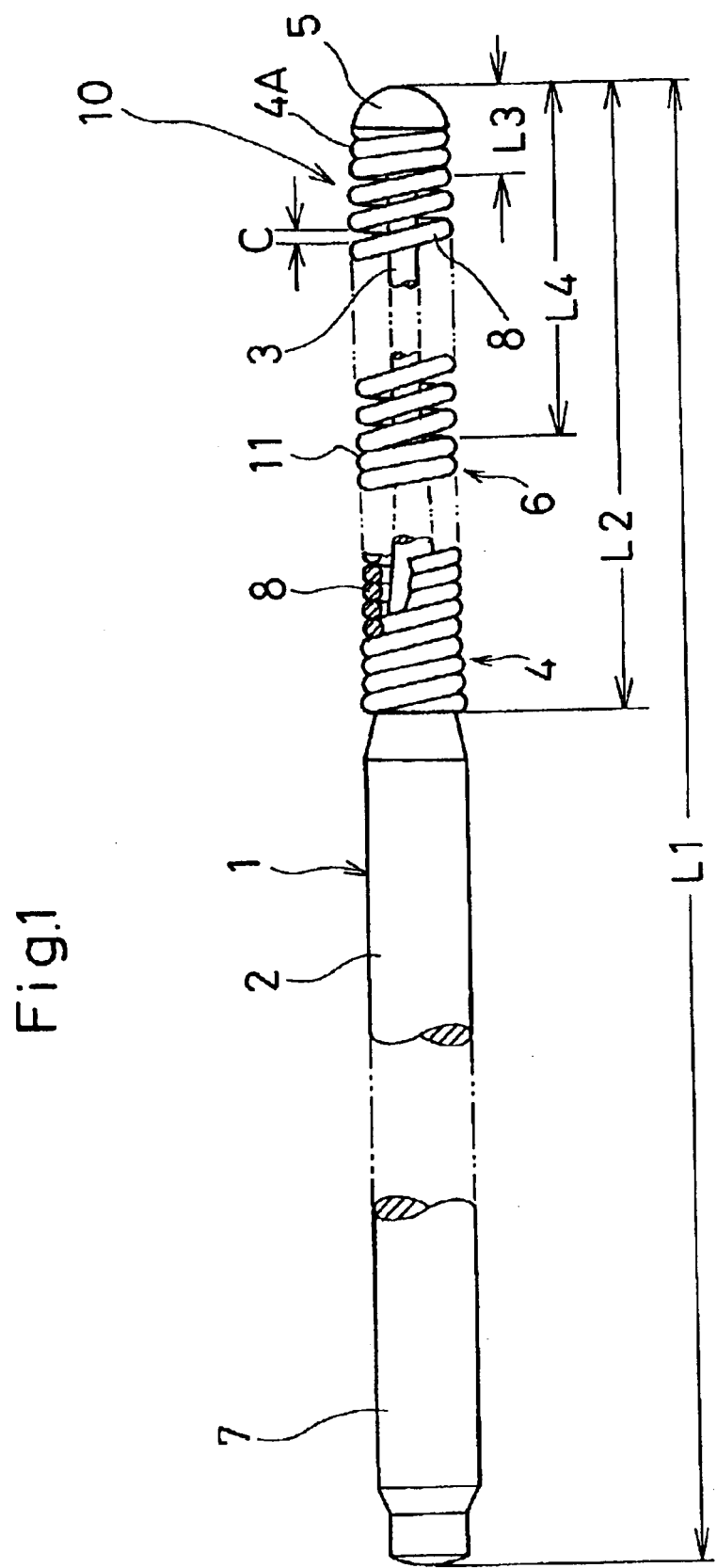
FIG. 1 is a side elevational view of a medical guide wire according to a first embodiment of the invention.
Figure 2:
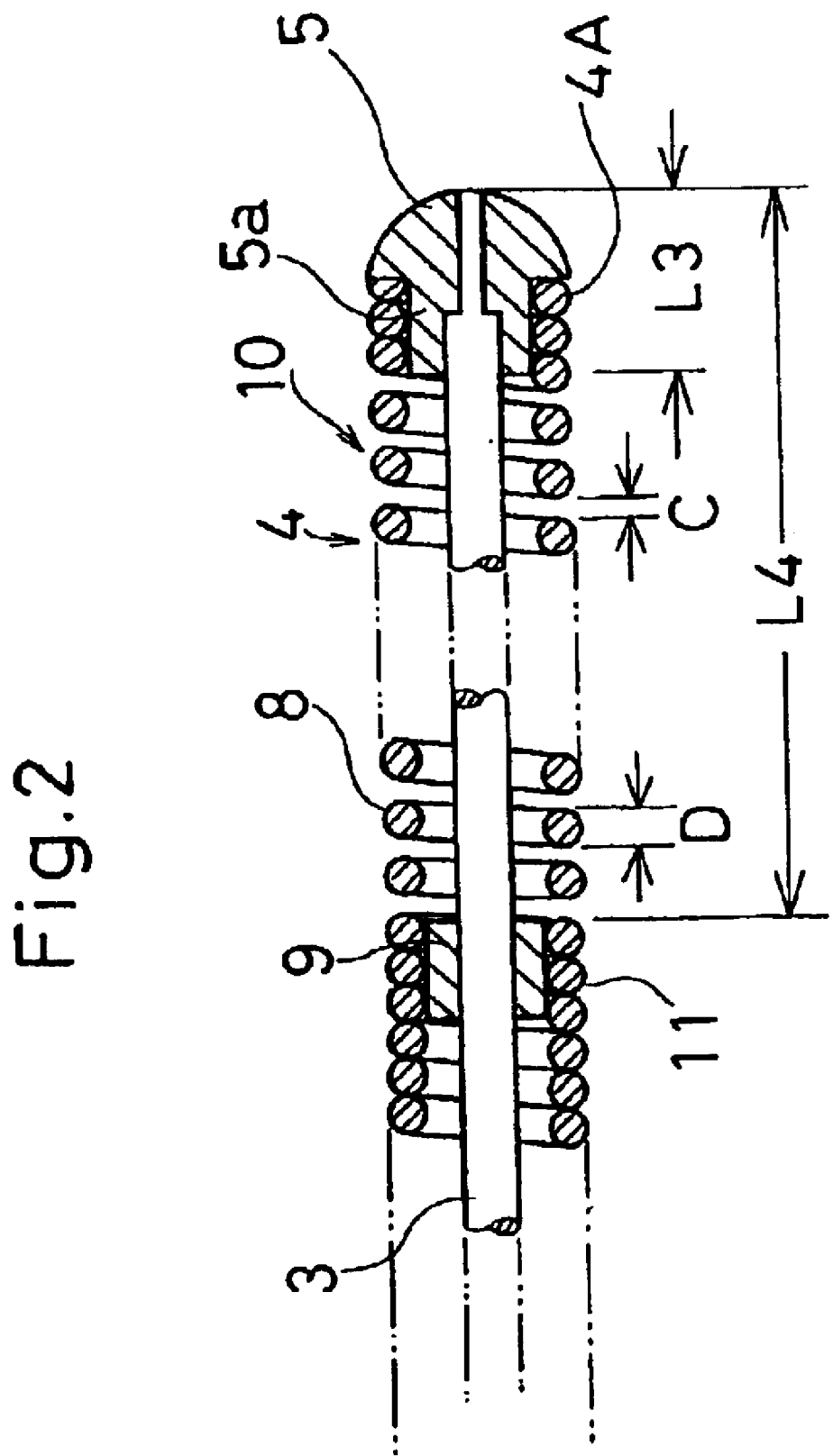
FIG. 2 is a longitudinal cross sectional view of a main part of the medical guide wire.

Referring to FIGS. 1 through 8 which show a medical guide wire 1 (referred to merely as "guide wire" hereinafter) according to a first embodiment of the present invention, a core line 3 is formed by thinning a distal end of a main wire portion 2 of a flexible line wire as shown in FIGS. 1 and 2. To a distal end of the core line 3, a spherical or semi-spherical head plug 5 is secured which has a stem portion 5a extended in one piece from a rear surface of the semi-spherical head. Around the core line 3, a helical spring 4 is provided. A front end of the helical spring 4 is firmly interfit to the stem portion 5a of the head plug 5 to have a leading end portion 6 superior in flexibility. In a front distal portion 10 including the head plug 5 and a part of the helical spring 4 extending from the head plug 5, two or three turns of the helical spring 4 is secured to the stem portion 5a of the head plug 5, a length L3 of a rigid portion 4A is 0.5 mm or less which extends from a top of the head plug 5 to a rear end of a portion in which the helical spring 4 is secured to the stem portion 5a. The helical spring 4 has an intermediary location 11 which is fixed to an intermediary boss portion 9 provided with an intermediary portion of the core line 3 so as to provide a loosely wound portion 8 which has a clearance C between the line element turns elastically expandable in the lengthwise direction when an outer force is applied to the loosely wound portion 8.

In this instance, an outer diameter of the helical spring 4 is 0.355 mm, a line diameter D of the helical spring 4 is 0.072 mm, the clearance C at free state is 0.021 mm (approximately 30% of the diameter D), an entire length L1 of the guide wire 4 is approximately 1800 mm, an entire length L2 of the helical spring 4 is approximately 300 mm, a width of the intermediary boss portion 9 is approximately 0.8 mm, and a length L4 from the top of the head plug 5 to the intermediary location 11 is approximately 24 mm.

The helical spring 4 is welded to the head plug 5 and the intermediary boss portion 9 by means of a TIG welding, laser spot welding or ball-shaped tin soldering material (Sn) (0.2~0.3 mm in dia.) in an aim to prevent a metal filler and flux from being dispersed during the welding operation.

Figure 3:
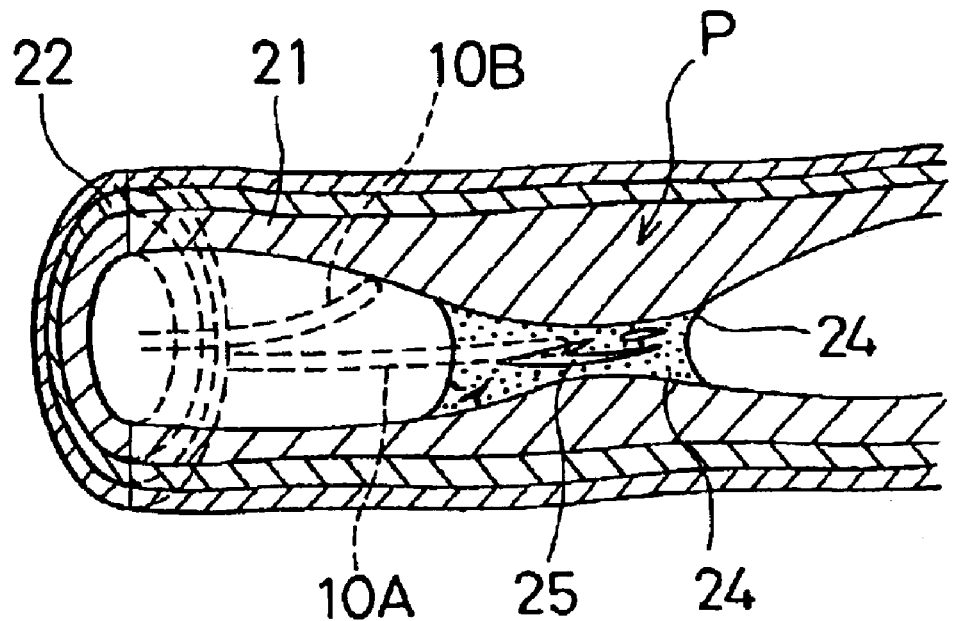
FIG. 3 is an explanatory view showing the medical guide wire when it is inserted into a blood vessel.

In the guide wire 1, the rigid portion 4A which forms a front end of the front distal portion 10 is exceedingly reduced its length to 0.5 mm, and the loosely wound portion 8 extended rearward from the rigid portion 4A is elastically expandable to vary the clearence C between the line element turns when an outer force is applied the loosely wound portion 8. For this reason, the loosely wound portion 8 has an elastically workable section which enables a manipulator to perceive at a handling knob 7 by the manner how the front distal portion 10 is in contact with an angiostenosis area P (referred simply to as "obstruction area P" hereinafter). The obstruction area P metamorphoses into fibrous tissue as the thrombus is progressively organized as shown in FIG. 3. The thrombus is organized faster at both end of the obstruction area P than a central area of the obstruction area P. Calcium salt and precipitate-related matters deposit on both the ends of the obstruction area P to harden them by calcification. As the thrombus is organized, a small blood vessel 25 (0.2 m or less in dia.) appears within the thrombus to permit a blood flow which communicate a left side lumen with a right side lumen across the thrombus.

The obstruction area P thus calcified and hardened, becomes concaved in shape at both ends with the small blood vessel 25 developed within the thrombus. With the preshaped front distal portion 10 in contact with the obstruction area P, the concaved shape of the obstruction area P can be perceived to judge whether or not the obstruction area P should be pierced based on the visual confirmation on the monitored image through the angiography and the feeling transmitted to the manipulator from the handling knob 7.

Since the front distal portion 10 is especially good in pliability, a difference in hardness between the normal intima 21 of the blood vessel and the calcified obstruction area P changes a bending degree of the front distal portion 10 depending on which portion of the obstruction area P the front distal portion 10 meets, as shown at 10B in FIG. 3. This enables the manipulator to judge the manner how the front distal portion 10 is in contact with the obstruction area P based on the feeling transmitted from the handling knob 7.

When the front distal portion 10 advances into a collagen fiber tissue 24 of the obstruction area P, and moved in a push and pull direction, the loosely wound portion 8 admits the collagen fiber tissue 24 into the clearance C. The change of resistance caused from the push and pull movement of the front distal portion 10 enables the manipulator to perceive whether or not the front distal portion 10 positions normally in the true lumen. Upon treating the obstruction area P, the front distal portion 10 is pushed and pulled repeatedly by 2~3 mm while confirming the postion in which the front distal portion 10 is located.

An outer surface of the small blood vessel 25 has a thin striated layer, around which the soft collagen fiber tissue 24 is formed, and the front distal portion 10 is likely introduced into the collagen fiber tissue 24 due to a limited resistance against the collagen fiber tissue 24, thus enabling the manipulator to advance the front distal portion 10 to pierce through the true lumen without being led astray into the false lumen as shown at 10A in FIG. 3. This is opposite to the prior art in which the extended rigid portion is often led astry into the false lumen because the rigid portion fails to follow the softness of the collagen fiber tissue 24.

Figure 4:
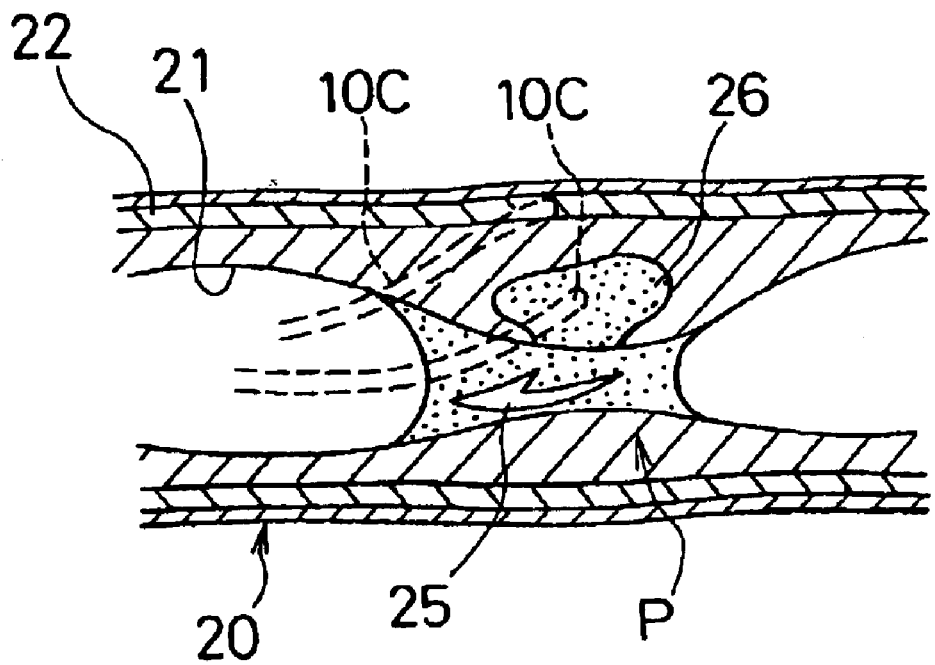
FIG. 4 is another explanatory view showing the medical guide wire when it is inserted into the blood vessel.
Figure 5:
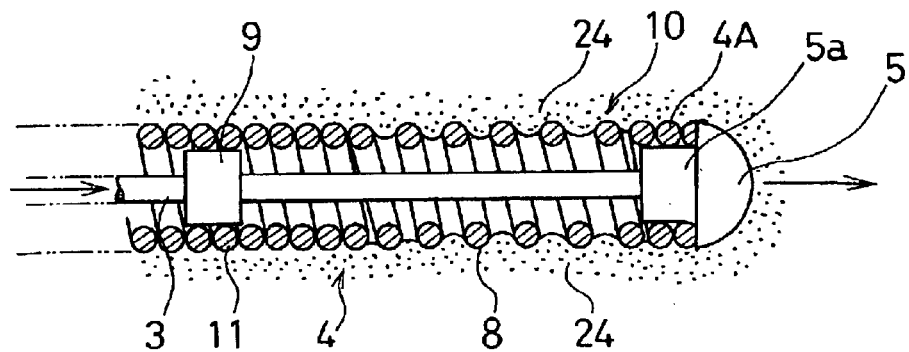
FIG. 5 is a longitudinal cross sectional view of a front distal portion inserted into a diseased area of the blood vessel.
Figure 6:
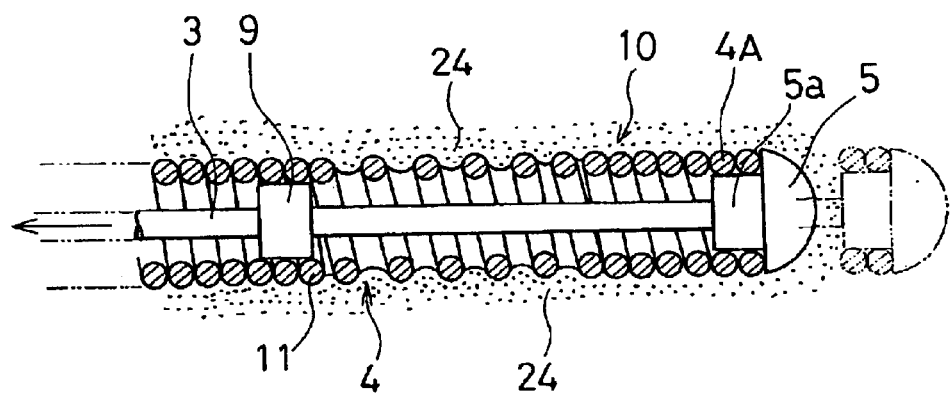
FIG. 6 is another longitudinal cross sectional view of the front distal portion inserted into the diseased area of the blood vessel.
Figure 7:
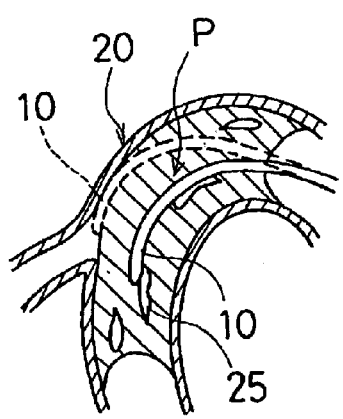
FIG. 7 is an explanatory view showing the medical guide wire when it is inserted into the blood vessel.
Figure 8:
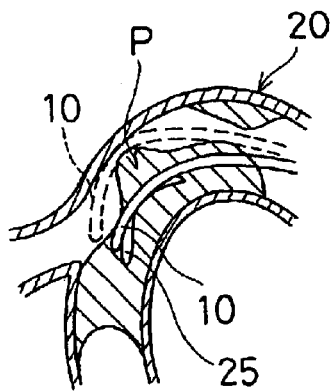
FIG. 8 is another explanatory view showing the medical guide wire when it is inserted into the blood vessel.

In the case in which the front distal portion 10 pierces through the intima 21 (false lumen) as shown at 10C in FIG. 4, the false lumen is perceived by an abnormal resistance felt when advancing the front distal portion 10 through endothelium cells of the intima 21 and encounters an atheroma 26 which is to develop into the thrombus.

When the front distal portion 10 passes through the intima 21 and advances into the media 22 which is formed by the smooth muscle and the elastic fibers, a sticky resistance is uniquely felt when the front distal portion 10 is pulled. The sticky resistance is positively transmitted to the manipulator so that the manipulator advances the front distal portion 10 into an abnormal position. Namely, by pushing and pulling the front distal portion 10 with the loosely wound portion 8 advanced into the media 22, the loosely wound portion 8 admits the collagen fiber tissue 24 into the clearance C to change the degree of resistance against collagen fiber tissue 24 as understood from FIGS. 5 and 6. Therefore, the guide wire 1 is effective in assisting to introduce the front distal portion 10 into the obstruction area P as well as to prevent the front distal portion 10 from being led astray into the false lumen.

The guide wire 1 is particularly effective in introducing the front distal portion 10 into a bifurcated and turned portion of the blood vessel 20. When the obstruction area P appears on the bifurcated and turned portion of the blood vessel 20, while the prior rigid portion is likely led astry into the false lumen as shown at broken lines in FIGS. 7 and 8, the front distal portion 10, however, favorably follows along the bifurcated and turned portion of the blood vessel 20 due to its good pliability and the preshaped tip provided with the front distal portion 10.

The length L4 of the highly pliable front distal portion 10 is approximately 24 mm so that the front distal portion 10 is positively useful for the obstruction area P of maximum length (approx. 15 mm) which is commonly observed in the most general diseased area. Because the welding between the helical spring 4 and the head plug 5 is due to the TIG welding or laser spot welding procedure in a protective atmosphere, the normal function of the front distal portion 10 is maintained and preventing an entry of foreign matters to avoid the very thin wire from being broken caused by the reduced strength.

Figure 9:
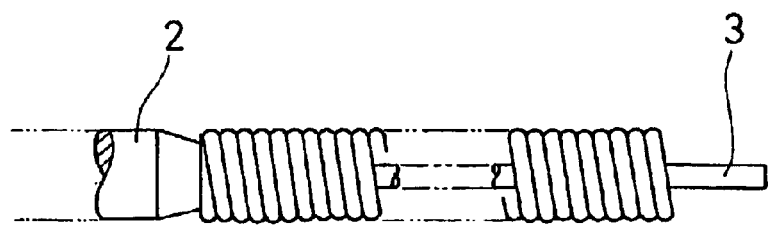
FIGS. 9~11 are sequential views showing how to manufacture the front distal portion of the medical guide wire.
Figure 10:
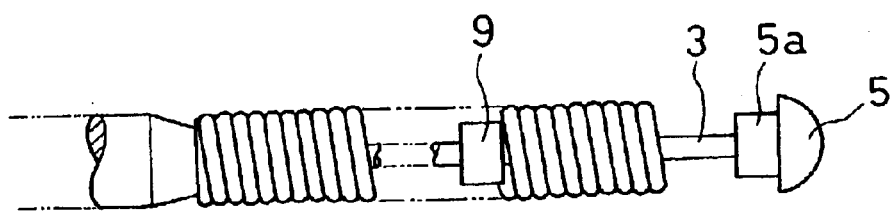
Figure 11:
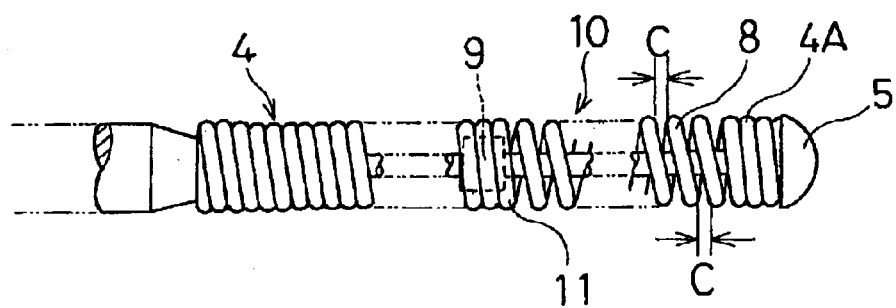

FIGS. 9~11 shows a method how to manufacture the head plug 5. The tightly wound helical spring is firstly provided around the core line 3, and the head plug 5 is secured to the tip of the core line 3 extended beyond the helical spring 4 with the use of a ball-shaped soldering material (0.2 mm in dia.) and its surface tension appeared when the ball-shaped soldering material is molten.

In this instance, a discrete head plug may be secured to the tip of the core line 3 by means of caulking. As other alternative, the tip of the core line 3 may be plastically deformed to define the head plug 5.

The front portion of the helical spring is, in some degree, expanded to interfit its two or three turns to the stem portion 5a of the head plug 5, and the soldering, TIG welding or laser spot welding is applied to the portion in which the helical spring 4 is fixedly secured to the stem portion 5a with the dispersion of the filler metal or flux prevented during the welding operation.

Thereafter, the clearance C between the line element turns of the loosely wound portion 8 is determined, and the intermediary location 11 is soldered to the intermediary boss portion 9 which is provided beforehand on the core line 3.

Upon welding the helical spring 4 and the head plug 5 to form the rigid portion 4A within 0.5 mm, in length, the ball-shaped soldering material (0.2 mm in dia.) may be used instead of the TIG welding or laser spot welding. In this instance, the method includes forming the plug head 5 by welding the core line 3 and helical spring 4 with the soldering material, and by bulging the core line 3 by applying the laser spot welding or TIG welding to the core line 3 and helical spring 4.

Figure 12:
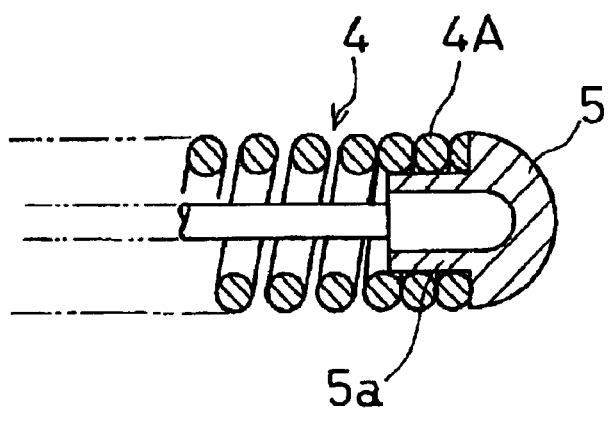
FIG. 12 is a longitudinal cross sectional view of a head plug according to a second embodiment of the invention.
Figure 13:
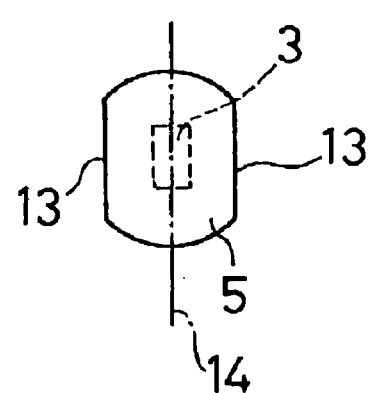
FIG. 13 is a plan view of the head plug of FIG. 12.

FIGS. 12 and 13 show a second embodiment of the invention in which right and left sides of the spherical portion of the head plug 5 are symmetrically undercut along a central line 14 to form flat portions 13 in a parallel direction. The flat portions 13 enable the head plug 5 to an enhanced directional maneuverability when the handling knob 7 is operated. In order to further enhance the directional maneuverability, the flat portions 13 are positioned out of the parallel but arranged such as to render the head plug 5 tapered off in the axial direction. Otherwise, it is preferable that the flat portions 13 are positioned in parallel with longer sides of the core line 3 which is formed rectangular in cross section.

Figure 14:
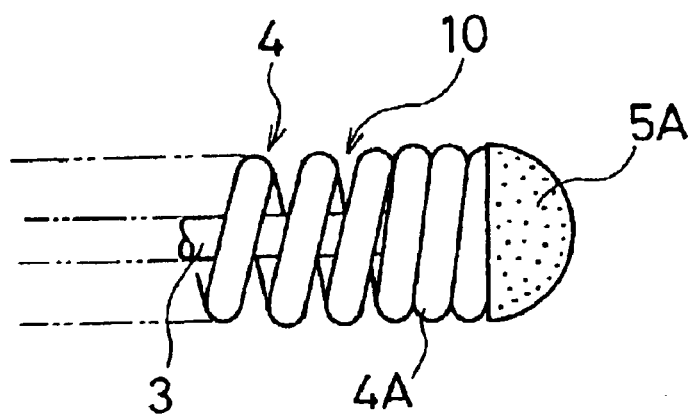
FIG. 14 is a longitudinal cross sectional view of a head plug according to a third embodiment of the invention.
Figure 15:
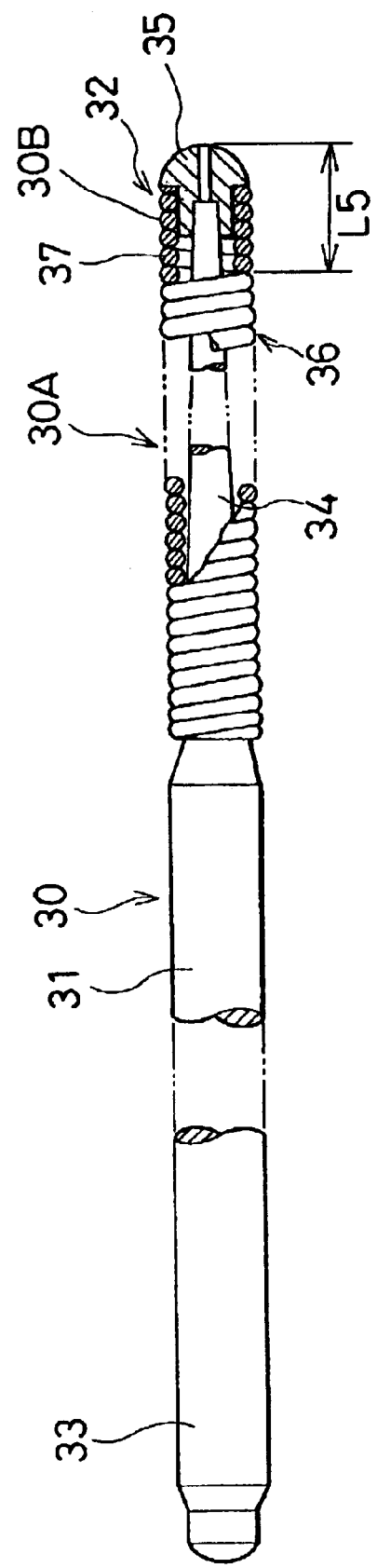
FIG. 15 is a side elevational view of a prior art medical guide wire but partially sectioned.
Figure 16:
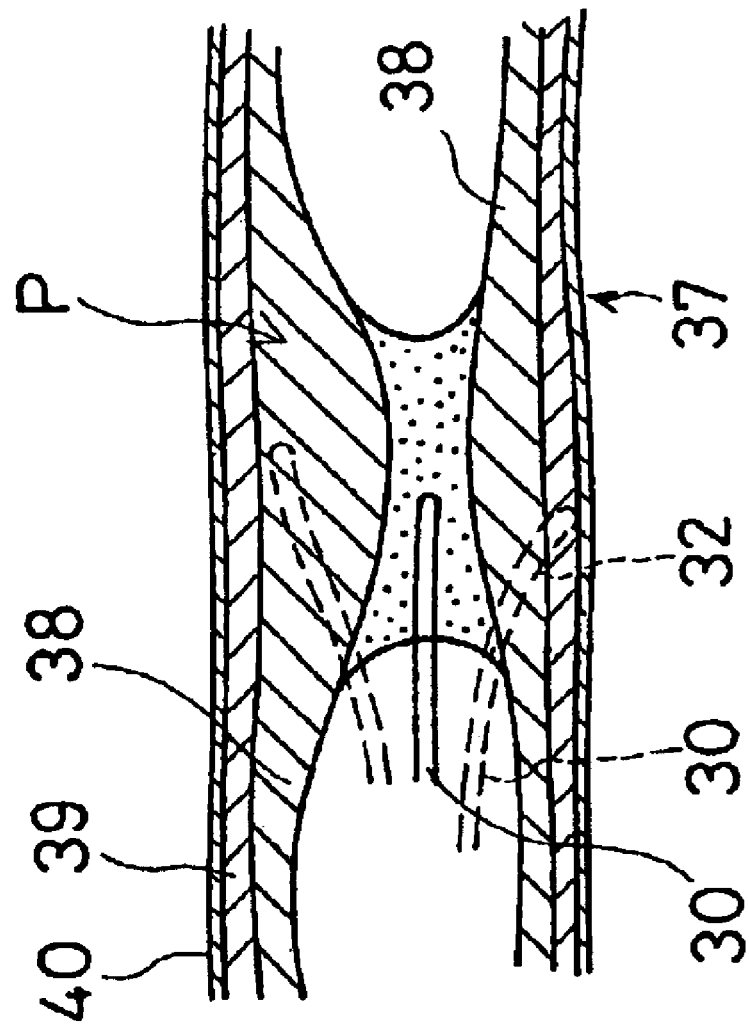
FIG. 16 is an explanatory view showing the prior art medical guide wire when it is inserted into a blood vessel.

FIG. 14 shows a third embodiment of the invention in which an outer surface of a head plug 5A is roughened instead of machining a mirror finish. The roughened surface of the head plug 5A enables the manipulator to feel an increase contact resistance against the obstruction area P so as to improve an operable feeling.

What is claimed is:

1. A medical guide wire comprising a flexible line wire having a main wire portion, a core line member and a helical spring provided around a distal end of said core line member, a front end of said helical spring being fixedly interfit to a head plug provided at a tip of said core line member;

a rigid portion located on a front end of aid helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define loosely wound portion as an elastically expandable portion from a rear end of said head plug to said intermediary location;

a clearance between line element turns of said loosely wound portion being within a range of 10–30% of a line diameter of said helical spring; and said loosely wound portion being approximately 24 mm in length.

2. A medical guide wire comprising a flexible line wire having a main wire portion, a core member and a helical spring provide around a distal end of said core line member, a front end of said helical spring being fixedly interfit to a head plug provided a tip of said core line member;

a rigid portion located on a front end of said helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define a loosely wound portion as an elastically expandable portion from a rear end of said head plug to said intermediary location; and said head plug forming a spherical or semi-spherical configuration, and a right and left side portions of said head plug being undercut to form flat surface portions.

3. The medical guide wire according to claim 2, wherein said core line member is rectangular in cross section, longer sides of which position in parallel with said flat surface portions of said head plug.

4. The medical guide wire according to claim 2, wherein said front end of said helical spring and said head plug are produced from TIG or laser spot welding.

5. A medical guide wire comprising a flexible line wire having a main wire portion, a core member and a helical spring provided around a distal end of said core line member, a front end of said helical spring being fixedly interfit to a head plug provided at a tip of said core line member;

a rigid portion located on a front end of said helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define a loosely wound portion as an elastically expandable portion from a rear end of said head plug to said intermediary location;

said loosely wound portion being approximately 24 mm in length; and said head plug forming a spherical or semi-spherical configuration, and a right and left side portions of said head plug being undercut to form flat surface portions.

6. The medical guide wire according to claim 5, wherein said core line member is rectangular in cross section, longer sides of which position in parallel with said flat surface portions of said head plug.

7. A medical guide wire comprising a flexible line wire having a main wire portion, a core member and a helical spring provided around a distal end of said core line member, a front end of said helical spring being fixedly interfit to a head plug provided at a tip of said core line member;

a rigid portion located on a front end of said helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define a loosely wound portion as an elastically expandable portion from a rear end of said head plug to said intermediary location;

said head plug forming a spherical or semi-spherical configuration, and right and left side portions of said head plug being undercut to form flat surface portions;

said core line member being rectangular in cross section, longer sides of which position parallel with said flat surface portions of said head plug; and said front end of said helical spring and said head plug being produced from TIG or laser spot welding.

8. A medical guide wire comprising a flexible line wire having a main wire portion, a core member and a helical spring provided around a distal end of said core line member, a front end of said helical spring being fixedly interfit to a head plug provided at a tip of said core line member;

a rigid portion located on a front end of said helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define a loosely wound portion as an elastically expandable portion from a rear end of said head plug to said intermediary location;

said loosely wound portion being approximately 24 mm in length;

said head plug forming a spherical or semi-spherical configuration, and right and left side portions of said head plug being undercut to form flat surface portions; and said front end of said helical spring and said head plug are produced from TIG or laser spot welding.

9. A medical guide wire comprising a flexible line wire having a main wire portion, a core member and a helical spring provided around a distal end of said core line member, a front end of said helical spring being fixedly interfit to a head plug provided at a tip of said core line member;

a rigid portion located on a front end of said helical spring, said rigid portion measuring 0.5 mm or less which extends lengthwisely from a top end of said head plug to a rear end of a portion in which said helical spring is fixed to said head plug, and an intermediary location is determined on an intermediary portion of said helical spring in which an intermediary boss portion is secured to said core line member to define a loosely wound portion as an elastically expandable portion from a rear end of said head plug to said intermediary location;

said loosely wound portion being approximately 24 mm in length;

said head plug forming a spherical or semi-spherical configuration, and left side portions of said head plug being undercut to form flat surface portions;

said core line member being rectangular in crosss section, longer sides of which position parallel with said flat surface portions of said head plug; and said front end of said helical spring and said head plug being produced from TIG or laser spot welding.

\* \* \* \* \*